US009781936B2

(12) United States Patent
Santra et al.

(10) Patent No.: US 9,781,936 B2
(45) Date of Patent: Oct. 10, 2017

(54) COMPOSITIONS, METHODS OF MAKING A COMPOSITION, AND METHODS OF USE

(71) Applicant: University of Central Florida Research Foundation, Inc., Orlando, FL (US)

(72) Inventors: Swadeshmukul Santra, Orlando, FL (US); Mikaeel Young, Oviedo, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 14/049,732

(22) Filed: Oct. 9, 2013

(65) Prior Publication Data

US 2015/0098974 A1    Apr. 9, 2015

(51) Int. Cl.
*A01N 59/20* (2006.01)

(52) U.S. Cl.
CPC ........... *A01N 59/20* (2013.01); *Y10S 977/773* (2013.01)

(58) Field of Classification Search
CPC .................................................... A01N 59/20
See application file for complete search history.

(56) References Cited

U.S. PATENT DOCUMENTS

| | | | |
|---|---|---|---|
| 2,913,419 A | 4/1956 | Alexander | |
| 3,983,214 A | 9/1976 | Misato et al. | |
| 3,992,146 A | 11/1976 | Fazzalari | |
| 4,440,746 A * | 4/1984 | Maglio | 514/86 |
| 5,252,542 A * | 10/1993 | Allan | 504/323 |
| 5,462,738 A | 10/1995 | LeFiles et al. | |
| 5,762,959 A * | 6/1998 | Soon-Shiong | A61K 9/1652 424/422 |
| 5,939,357 A | 8/1999 | Jones et al. | |
| 6,471,976 B1 * | 10/2002 | Taylor et al. | 424/409 |
| 6,548,264 B1 | 4/2003 | Tan et al. | |
| 6,924,116 B2 | 8/2005 | Tan et al. | |
| 7,147,921 B2 | 12/2006 | Camp et al. | |
| 7,163,709 B2 | 1/2007 | Cook et al. | |
| 7,226,610 B2 | 6/2007 | Winniczuk | |
| 7,332,351 B2 | 2/2008 | Tan et al. | |
| 8,221,791 B1 * | 7/2012 | Santra | 424/484 |
| 8,246,933 B2 | 8/2012 | Jiang et al. | |
| 8,361,437 B2 | 1/2013 | Sharma et al. | |
| 2001/0051174 A1 | 12/2001 | Staats | |
| 2003/0032669 A1 * | 2/2003 | Verbruggen et al. | 514/479 |
| 2004/0067247 A1 | 4/2004 | De Sloovere et al. | |
| 2004/0091417 A1 | 5/2004 | Yadav | |
| 2005/0002996 A1 * | 1/2005 | Sojka | 424/445 |

(Continued)

OTHER PUBLICATIONS

T Naganuma, Y Kagawa. "Effect of particle size on the optically transparent nano meter-order glass particle-dispersed epoxy matrix composites." Composites Science and Technology, vol. 62, 2002, pp. 1187-1189.*

(Continued)

*Primary Examiner* — Isaac Shomer
(74) *Attorney, Agent, or Firm* — Arent Fox LLP

(57) ABSTRACT

Embodiments of the present disclosure, in one aspect, relate to compositions including a copper/silica nanocomposite and a polymer, methods of making a composition, methods of using a composition, and the like.

16 Claims, 18 Drawing Sheets

(56) References Cited

U.S. PATENT DOCUMENTS

| | | |
|---|---|---|
| 2005/0084438 A1 | 4/2005 | Do et al. |
| 2006/0018966 A1 | 1/2006 | Lin |
| 2007/0009672 A1 | 1/2007 | Jeong et al. |
| 2007/0068824 A1* | 3/2007 | Payne .................... C25D 5/022 205/317 |
| 2007/0098806 A1 | 5/2007 | Ismail et al. |
| 2010/0015236 A1 | 1/2010 | Magdassi et al. |
| 2011/0065582 A1* | 3/2011 | Undabeytia Lopez et al. ............................ 504/234 |

OTHER PUBLICATIONS

YH Kim, DK Lee, HG Cha, CW Kim, YC Kang, YS Kang. "Preparation and Characterization of the Antibacterial Cu Nanoparticle Formed on the Surface of SiO2 Nanoparticles." Jounal of Physical Chemistry B, vol. 110, 2006, pp. 24923-24928.*
LR Khot, S Sankaran, JM Maja, R Ehsani, EW Schuster. "Applications of nanomaterials in agricultural production and crop protection: A review." Crop Protection, vol. 35, 2012, pp. 64-70.*
S Dubey, V Jhelum, PK Patanjali. "Controlled Release Agrochemicals Formulations: A Review." Journal of Scientific & Industrial Research, vol. 70, Feb. 2011, pp. 105-112.*
R Casiday and R Frey. "Acid Rain Inorganic Reactions Experiment." http://www.chemistry.wustl.edu/~edudev/LabTutorials/Water/FreshWater/acidrain.html, accessed by examiner on Nov. 30, 2016, 7 printed pages.*
Tae-Gon Kim, et al. Silver-Nanoparticle Dispersion From the Consolidation of Ag-Attached Silica Colloid, School of Materials Science and Engineering, Seoul National University, Seoul 151-744, Korea, Oct. 4, 2003, 8 pages.
Yeshchenko, Oleg, Influence of Annealing Conditions on Structure and Optical Properties of Copper Nanoparticles Embedded in Silica Matrix, 2006, Physics Department, National Taras Shevchenko Kyiv University, Ukraine, pp. 1-25.
Kikteva, T.A., Probing the Sol-Gel Conversion in the Tetraethoxysilane/Alcohol/Water System with the Aid of Diffusion-Controlled Flourescence Quenching, 1997, Journal of Colloid and Interface Science, vol. 193, pp. 163-166.
Cho. et al.. "The Study of Antimicrobial Activity and Preservative Effects of Nanosilver Ingredient". Electrochimica Acta 51,956-960 (2005).
Feng, et al. "A Mechanistic Study of the Antibacterial Effect of Silver Ions on *Escherichia coli* and *Staphylococcus aureus*", Journal of Biomedical Materials Research 52, 662-668 (2000).
Jasiorski, et al., "Textile with silver Silica Spheres: its Antimicrobial Activity against *Escherichia coli* and *Staphylococcus aureus*", Journal of Sol-Gel Science and Technology 51, 330-334 (2009).
Lu, et al., "A Simple and Effective Route for the Synthesis of Crystalline Silver Nanrods and Nanowires", Advanced Functional Materials 14, 183-189 (2004).
Solomon, et al. (2007). "Synthesis and study of silver nanoparticles." Journal of Chemical Education. 84, 322-325.
Pal, et al. (2007). "Does the antibacterial activity of silver nanoparticles depend on the shape of the nanoparticle? A study of the gram-negative bacterium *Escherichia coli*." Applied Environmental Microbiology 73, 1712-1720.
Jung, et al. (2008). Antibacterial activity and mechanism of action of the silver ion in *Staphylococcus aureus* and *Escherichia coli*. Applied Environmental Microbiology 74, 2171-2178.
Frisken, B. J. (2001 ). "Revisiting the method of cumulants for the analysis of dynamic light-scattering data." Applied Optics 40, 4087-4091.
Schillinger, et al. (1989). "Antibacterial Activity of Lactobacillus-Sake Isolated from Meal." Applied and Environmental Microbiology 55, 1901-1906.
Rastogi, et al., "Ag colloids and Ag clusters over EDAPTMS-coated silica nanoparticles:synthesis, characterization, and antibacterial activity against *Escherichia coli*." Nanomedicine-Nanotechnology Biology and Medicine 7, 305-314 (2011 ).
Collins, T.J., "ImageJ for Microscopy Biotechniques." 43, 25-30(2007).
Naik, et al., "Biomimetic synthesis and patterning of silver nanoparticles." Nature Materials 1, 169-172 (2002).
Mock, et al., "Shape effects in plasmon resonance of individual colloidal silver nanoparticles." Journal of Chemical Physics 116, 6755-6759 (2002).
Manipradad, et al.; Novel Copper (Cu) Loaded Core-Shell Silica Nanoparticles with Improved Cu Bioavailability: Synthesis, Characterization and Study of Antibacterial Properties; Journal of Biomedical Nanotechnology; vol. 8, 1-9, 2012.
Maniprasad, et al.; Antimicrobial Properties of Copper and Silver Loaded Silica Nanomaterials; Manuscript ID No. 1198620; to be submitted to the 36th International Conference on Advanced Ceramics and Composites (ICACC); Apr. 4, 2012.
H.W. Richardson, "Handbook of Copper Compounds and Applications" Copper Fungicides/batericides H.W. Richardson Editor, 1997, Marcel Dekker, Inc.: New York, NY, pp. 93-122.
Torgeson D.C .. ed. "Fungicides—An Advanced Treatise" Agricultural and Industrial Applications and Enviromental Interaction. vol. 1. 1967. Academic Press: New York. NY, Ch. 6, p. 153-193 [chapter Title: Formulation: Author: E. Somers.
Navarro, E., et al., in "Environmental behavior and ecotoxicity of engineered nanoparticles to algae, plants, and fungi," Ecotoxicology, 2008, 17(5): pp. 372-386.
Oberdorster, G., et al., in Nanotoxicology: An Emerging Discipline Evolving from Studies of Ultrafine Particles, Environmental Health Perspectives, 2005, 113(7): pp. 823-839.
S. Santra, et al., in "Fluorescence Lifetime Measurements to Determine the Core-Shell Nanostructure of FITC-doped Silica Nanoparticles: An Optical Approach to Evaluate Nanoparticle Photostability" Journal of Luminescence, 2006, 117(1) pp. 75-82.
Zhang, K., Synthesis and Characterization of Silica-Copper Oxide Composite Derived from Microemulsion Processing, 1999, Langmuir, vol. 15, pp. 3056-3061.
Zhang, X. A New Solution Route to Hydrogen-terminated Silicon Nanoparticles: Synthesis, Functionalization and Water Stability, Jan. 2007, Nanotechnology, vol. 18, pp. 1-6.
The International Search Report and Written Opinion dated Jan. 2, 2011.
Kim, Y.H., et al., "Preparation and characterization of the Antibacterial Cu Nanoparticle Formed on the Surface of Si02 Nanoparticles," J. Phys. Chem B 2006, vol. 110, pp. 24923-24928.
Barik, T.K., et al., "Nanosilica—From MEdicine to Pest Control," Parasitol, R es 2008, vol. 103, pp. 253-258.
Sebastien Dugravot et al. Dimethyl Disulfide Exerts Insecticidal Neurotoxicity Through Mitochondrial Dysfunction and Activation of Insect KATP Channels; Journal of Neurophysiology; 2003; 8 pages.

* cited by examiner

Figure 22

| Formula | Concentration (ppm) | Phytotoxicity Studies (hrs) | | | Conditions Adequate (≥80F, ≥40% Hum) |
|---|---|---|---|---|---|
| | | 24 | 48 | 72 | |
| Kocide 3000 | 450 | - | - | - | Yes |
| Kocide 3000 | 700 | - | - | - | Yes |
| Kocide 3000 | 900 | - | - | - | Yes |
| SG0001 | 450 | - | - | - | Yes |
| SG0001 | 900 | - | + | ++ | Yes |
| SG0005 | 450 | - | - | - | Yes |
| SG0005 | 900 | - | + | + | Yes |
| SG0015 | 450 | - | - | + | Yes |
| SG0015 | 700 | + | + | + | Yes |
| SG0015 | 900 | + | + | ++ | Yes |
| SG0017 | 450 | - | - | + | Yes |
| SG0017 | 700 | + | + | + | Yes |
| SG0017 | 900 | + | + | ++ | Yes |
| SG0018 | 700 | - | - | + | Yes |
| SG0018 | 900 | + | + | ++ | Yes |

Figure 23

| Formula | Concentration (ppm) | Phytotoxicity Studies (hrs) | | | Conditions Adequate (≥80F, ≥40% Hum) |
|---|---|---|---|---|---|
| | | 24 | 48 | 72 | |
| SG0020 | 300 | - | - | - | Yes |
| SG0020 | 500 | - | - | + | Yes |
| SG0020 | 700 | - | + | ++ | Yes |
| SG0021 | 300 | - | - | - | Yes |
| SG0021 | 500 | - | - | + | Yes |
| SG0021 | 700 | + | + | ++ | Yes |
| SG0022 | 300 | - | - | - | Yes |
| SG0022 | 500 | - | - | - | Yes |
| SG0022 | 700 | - | + | + | Yes |

Figure 24

| Formula | Concentration (ppm) | Phytotoxicity Studies (hrs) | | | Conditions Adequate (≥80F, ≥40% Hum) |
|---|---|---|---|---|---|
| | | 24 | 48 | 72 | |
| SG0022M | 500 | - | - | - | Yes |
| SG0022M | 700 | - | - | - | Yes |
| SG0022M | 900 | - | - | - | Yes |
| SG0023 | 500 | - | - | - | Yes |
| SG0023 | 700 | - | - | - | Yes |
| SG0023 | 900 | - | - | - | Yes |
| SG0024 | 500 | - | - | - | Yes |
| SG0024 | 700 | - | - | - | Yes |
| SG0024 | 900 | - | - | - | Yes |

Figure 25

| Santra Group Code (SG) | Inactive Ingredient | pH | MIC in metallic Cu (µg/mL) |
|---|---|---|---|
| Kocide 3000 | NA | 8.6 | 1000 |
| 0001 | PAAm | 4.05 | 437.5 |
| 0005 | PAAm | 4.08 | 437.5 |
| 0015 | PVP | 4.2 | 437.5 |
| 0017 | PAAm | 4.08 | 437.5 |
| 0018 | PVP | 4.2 | 437.5 |
| 0020 | PAAm | 3.8 | 500 |
| 0021 | PAAm | 3.75 | 500 |
| 0022 | PAAm | 4.33 | 500 |
| 0022M | PAAm | 8.67 | 500 |
| 0023 | PAAm | 8.82 | 500 |
| 0024 | PVP | 8.38 | 500 |

COMPOSITIONS, METHODS OF MAKING A COMPOSITION, AND METHODS OF USE

BACKGROUND

The globalization of business, travel and communication brings increased attention to worldwide exchanges between communities and countries, including the potential globalization of the bacterial and pathogenic ecosystem. Bactericides and fungicides have been developed to control diseases in man, animal and plants, and must evolve to remain effective as more and more antibiotic, pesticide and insecticide resistant bacteria and fungi appear around the globe.

Bacterial resistance to antimicrobial agents has also emerged, throughout the world, as one of the major threats to both man and the agrarian lifestyle. Resistance to antibacterial and antifungal agents has emerged as an agricultural issue that requires attention and 20 improvements in the treatment materials in use today.

For example, focusing on plants, there are over 300,000 diseases that afflict plants worldwide, resulting in billions of dollars of annual crop losses. The antibacterial/antifungal formulations in existence today could be improved and made more effective.

SUMMARY

In accordance with the purpose(s) of the present disclosure, as embodied and broadly described herein, embodiments of the present disclosure, in one aspect, relate to compositions including a copper/silica nanocomposite and a polymer, methods of making a composition, methods of using a composition, and the like.

In an embodiment, a composition, among others, includes: a copper/silica nanocomposite having a silica gel matrix that includes copper from one or more of copper nanoparticles and copper ions, and a polymer selected from the group consisting of: polyacrylamide, polyvinyl alcohol, polyvinyl pyrolidone, polyethyleneimine, polyethylene glycol, polypropylene glycol, polyacrylic acid, dextran, chitosan, alginate, and a combination thereof.

In an embodiment, a method of making a composition, among others, includes: mixing a silica precursor compound, a copper precursor compound, and water; adjusting the pH to less than about 7 and holding for about 12 to 36 hours; forming a copper/silica nanocomposite having a silica gel matrix that includes copper from one or more of copper nanoparticles and copper ions; mixing a polymer with the mixture while having an acidic pH for about 12 to 36 hours, wherein the polymer is selected from the group consisting of: polyacrylamide, polyvinyl alcohol, polyvinyl pyrolidone, polyethyleneimine, polyethylene glycol, polypropylene glycol, polyacrylic acid, dextran, chitosan, alginate, and a combination thereof; raising the pH to about 4 to 10; and forming the composition.

In an embodiment, a method, among others, includes: disposing a composition on a surface, wherein the composition has a copper/silica nanocomposite having a silica gel matrix that includes copper from one or more of copper nanoparticles and copper ions, and a polymer selected from the group consisting of: polyacrylamide, polyvinyl alcohol, polyvinyl pyrolidone, polyethyleneimine, polyethylene glycol, polypropylene glycol, polyacrylic acid, dextran, chitosan, alginate, and a combination thereof; and killing a substantial portion of a microorganism or inhibiting or substantially inhibiting the growth of the microorganisms on the surface of a structure or that come into contact with the surface of the structure.

Other systems, methods, features, and advantages will be, or become, apparent to one with skill in the art upon examination of the following drawings and detailed description. It is intended that all such additional structures, systems, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 22 is a table that illustrates the phytotoxicity studies of SG0001, SG0005, SG0015, SG0017 and SG0018 at Cu concentrations of 450, 700 and 900 ppm. (−) No damage, (+) Moderate damage, (++) Heavy damage.

FIG. 23 is a table that illustrates the phytotoxicity studies of SG0020, SG0021 and SG0022 at Cu concentrations of 300, 500 and 700 ppm. (−) No damage, (+) Moderate damage, (++) Heavy damage.

FIG. 24 is a table that illustrates the phytotoxicity studies of SG0022M, SG0023 and SG0024 at Cu concentrations of 500, 700 and 900 ppm. (−) No damage, (+) Moderate damage, (++) Heavy damage.

FIG. 25 is a study that illustrates the minimum inhibitory concentration (MIC) of SG nanoformulations and Kocide 3000 against *E. coli* expressed in Cu concentration ((μg/mL).

DETAILED DESCRIPTION

Figure 1:
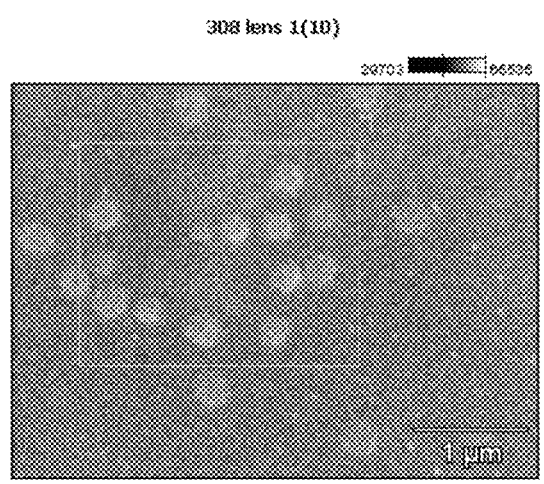
FIG. 1 illustrates spherical clusters of material within SG0023 seen in SEM.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

The term "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

The term "antibacterial characteristic" refers to the ability to kill and/or inhibit the growth of bacteria. A substance having an antibacterial characteristic may be harmful to bacteria. A substance having an antibacterial characteristic can kill the bacteria and/or prevent or substantially prevent the replication or reproduction of the bacteria.

"Uniform plant surface coverage" refers to a uniform and complete (e.g., about 100%) wet surface due to spray application of embodiments of the present disclosure. In other words, spray application causes embodiments of the present disclosure to spread throughout the plant surface.

"Substantial uniform plant surface coverage" refers to about 70%, about 80%, about 90%, or more uniform plant surface coverage.

"Substantially covering" refers to covering about 70%, about 80%, about 90%, or more, of the leaves and branches of a plant.

"Plant" refers to trees, plants, shrubs, flowers, and the like as well as portions of the plant such as twigs, leaves, stems, branches, fruit, flowers, and the like. In a particular embodiment, the term plant includes a fruit tree such as a citrus tree (e.g., orange tree, lemon tree, lime tree, and the like).

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. Alkyl can include alkyl, dialkyl, trialkyl, and the like.

As used herein, "treat", "treatment", "treating", and the like refer to acting upon a disease or condition with a composition of the present disclosure to affect the disease or condition by improving or altering it. In addition, "treatment" includes completely or partially preventing (e.g., about 70% or more, about 80% or more, about 90% or more, about 95% or more, or about 99% or more) a plant form acquiring a disease or condition. The phrase "prevent" can be used instead of treatment for this meaning. "Treatment," as used herein, covers one or more treatments of a disease in a plant, and includes: (a) reducing the risk of occurrence of the disease in a plant predisposed to the disease but not yet diagnosed as infected with the disease (b) impeding the development of the disease, and/or (c) relieving the disease, e.g., causing regression of the disease and/or relieving one or more disease symptoms.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Carnesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter species, Vibrio cholera, Ehrlichia species, Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other Enterobacteria, *Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae*.

The term "protozoan" as used herein includes, without limitations flagellates (e.g., *Giardia lamblia*), amoeboids (e.g., *Entamoeba histolitica*), and sporozoans (e.g., *Plasmodium knowlesi*) as well as ciliates (e.g., *B. coli*). Protozoan can include, but it is not limited to, *Entamoeba coli, Entamoeabe histolitica, Iodoamoeba buetschlii, Chilomastix meslini, Trichomonas vaginalis, Pentatrichomonas homini, Plasmodium vivax, Leishmania braziliensis, Trypanosoma cruzi, Trypanosoma brucei,* and *Myxoporidia*.

The term "algae" as used herein includes, without limitations microalgae and filamentous algae such as *Anacystis nidulans, Scenedesmus* sp., *Chlamydomonas* sp., *Clorella* sp., *Dunaliella* sp., *Euglena* sp., *Prymnesium* sp., *Porphyridium* sp., *Synechoccus* sp., *Botryococcus braunii, Clypthecodinium cohnii, cylindrotheca* sp., *Microcystis* sp., *Isochlysis* sp., *Monallanthus salina, M. minutum, Nannochloris* sp., *Nannochloropsis* sp., *Neochloris oleoabundans, Nitzschia* sp., *Phaeodactylum tricornutwn, Schizochytrium* sp., *Senedesmus obliquus*, and *Tetraseimis sueica* as well as algae belonging to any of *Spirogyra, Cladophora, Vaucheria, Pithophora* and *Enteromorpha* genera.

The term "fungi" as used herein includes, without limitations, a plurality of organisms such as molds, mildews and rusts and include species in the *Penicillium, Aspergillus, Acremonium, Cladosporium, Fusarium, Mucor, Nerospora, Rhizopus, Tricophyton, Botryotinia, Phytophthora, Ophiostoma, Magnaporthe, Stachybotrys* and *Uredinalis* genera.

Discussion:

In accordance with the purpose(s) of the present disclosure, as embodied and broadly described herein, embodiments of the present disclosure, in one aspect, relate to compositions including a copper/silica nanocomposite and a polymer, methods of making a composition, methods of using a composition, and the like. In an embodiment, the composition can be used as an antimicrobial agent to kill and/or inhibit the formation of microorganisms on a surface such as a tree, plant, and the like. An advantage of the present disclosure is that the composition is water soluble, non-phytotoxic, film-forming, and has antimicrobial properties. In particular, the combination of the copper/silica nanocomposite and a polymer in the composition provides for water soluble formulation that can form a film on a surface with enhanced adherence to other compositions not including the polymer, while not degrading the antimicrobial properties of the copper/silica nanocomposite.

In addition, embodiments of the present disclosure provide for a composition that can be used for multiple purposes. Embodiments of the present disclosure are advantageous in that they can slowly release one or more agents that can be used to prevent, substantially prevent and/or treat or substantially treat a disease or condition in a plant, act as an antibacterial and/or antifungal. Another advantage of an embodiment of the present disclosure is that the agent(s) can be controllably released over a long period of time (e.g., from the day of application until a few weeks or months (e.g., about 6 or 8 months)). Another advantage of the present disclosure is that the composition is substantially (e.g., greater than about 95% and about 99%) or completely transparent to visible light or translucent to visible light.

In an embodiment, the composition may have an antimicrobial characteristic (e.g., kills at least 70%, at least 80%, at least 90%, at least 95%, or at least 99% of the microorganisms (e.g., bacteria) on the surface and/or reduces the amount of microorganisms that form or grow on the surface by at least 70%, at least 80%, at least 90%, at least 95%, or at least 99%, as compared to a similar surface without the composition disposed on the surface). Additional details are described in the Examples.

In an embodiment, the composition can be disposed on a surface of a structure. In an embodiment, the structure can include plants such as trees, shrubs, grass, agricultural crops, and the like, includes leaves and fruit. In an embodiment, the composition provides uniform plant surface coverage, substantial uniform plant surface coverage, or substantially covers the plant. In an embodiment, the composition can be used to treat a plant having a disease or to prevent the plant from obtaining a disease.

In an embodiment, the structure can include those that may be exposed to microorganisms and/or that microorganisms can grow on, such as, without limitation, fabrics, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials. In an embodiment, the structure can include textile articles, fibers, filters or filtration units (e.g., HEPA for air and water), packaging materials (e.g., food, meat, poultry, and the like food packaging materials), plastic structures (e.g., made of a polymer or a polymer blend), glass or glass like structures on the surface of the structure, metals, metal alloys, or metal oxides structure, a structure (e.g., tile, stone, ceramic, marble, granite, or the like), and a combination thereof.

In an embodiment, the copper component can include a copper ion, metallic copper, copper oxide, copper oxychloride, copper sulfate, copper hydroxide, and a combination thereof. The copper component can include copper ions that are electrostatically bound to the silica nanoparticle core or amorphous silica matrix, copper covalently bound to the hydrated surface of the nanoparticle or amorphous silica matrix, and/or copper oxides and/or hydroxides bound to the surface of the nanoparticle or amorphous silica matrix. In an embodiment, the composition includes the copper component in two or in all three of these states.

In an embodiment, the copper component can be in a soluble (amorphous) and an insoluble (crystalline) form. By controlling the soluble and insoluble ratio, the release rate of the copper component can be controlled as a function of time. As a result, the release rate of the copper component can be controlled so that antibacterial and/or antifungal characteristics can be effective for time frames of days to weeks or to months. In other words, the copper component can be released from the multifunctional silica based nanoparticle or gel starting from the day of application and continuing release to about a week, about a month, about two months, about three months, about four months, about five months, about six months, about seven month, or about eight months. The ratio of the soluble to insoluble copper component can be adjusted to control the release rate. In an embodiment, the ratio of the soluble copper to the insoluble copper (e.g., Chelated Cu)$_X$ (Crystalline Cu)$_{1-X}$) can be out 0:1 to 1:0 (X can be about 0.1 to 0.99 or about 0.01 to 1), and can be modified in increments of about 0.01 to produce the ratio that releases the Cu for the desired period of time. Parameters that can be used to adjust the ratio include: solvent polarity and protic nature (i.e., hydrogen bonding capability), Cu nanoparticle precursor (e.g., Cu sulfate) concentration, temperature, concentration of silane precursor (such as tetraethylorthosilicate, TEOS), amount of polymer, type of polymer, and the like. In an embodiment, the copper nanoparticle precursor compound can be an insoluble Cu compounds (e.g., copper hydroxide, cupric chloride, cuprous chloride, cupric oxide, cuprous oxide), a soluble Cu compounds (e.g., copper sulfate, copper nitrate), or a combination thereof. In an embodiment, the silane nanoparticle precursor can be alkyl (C2 to C6) silane, tetraethoxysilane (TEOS), tetramethoxysilane (TMOS), sodium silicate, a silane precursor that can produce silicic acid or silicic acid like intermediates, or a combination thereof.

In an embodiment, the metallic copper can be about 1 microgram (μg)/mL to 20 milligram (mg)/mL weight percent, of the copper/silica-polymer nanocomposite.

"Silica gel matrix" or "silica nanogel matrix" refers to amorphous gel like substance that is formed by the interconnection of silica particles (e.g., nanoparticles (e.g., 2 to 500 nm or 5 to 50 nm)) to one another. In an embodiment, the amorphous silica gel has no ordered (e.g., defined) structure (opposite to crystalline structure) so an "amorphous gel" refers to gel material having amorphous structural composition. In an embodiment, the silica nanoparticles of the silica gel are interconnected covalently (e.g., through —Si—O—Si— bonds), physically associated via Van der Waal forces, and/or through ionic interactions (e.g., with copper ions).

In an embodiment, the silica particles are interconnected and copper nanoparticles can be disposed within the silica gel matrix and/or attached to one or more silica particles. In an embodiment, the copper nanoparticles are substantially (e.g., greater than about 80%, about 90%, about 95%, or about 99%) monodisperse. In an embodiment, the silica gel is disposed around the entire copper nanoparticle, which, although not intending to be bound by theory, causes the copper/silica nanocomposite to be transparent to visible light. Embodiments of the present disclosure include the appropriate ratio of silica gel to copper nanoparticle so that the nanocomposite is transparent to visible light, while also maintaining antimicrobial characteristics.

In an embodiment, the diameter of the particles (e.g., silica and/or copper) can be varied from a few nanometers to hundreds of nanometers by appropriately adjusting synthesis parameters, such as amounts of silane precursor, polarity of reaction medium, pH, time or reaction, and the like. For example, the diameter of the particles can be controlled by adjusting the time frame of the reaction. In an embodiment, the silica and copper nanoparticles can independently be about 2 to 25 nm or about 5 to 20 nm. In addition, the concentration of the copper ions can be appropriately adjusting synthesis parameters, such as amounts of silane precursor, polarity of reaction medium, pH, time or reaction, and the like.

As mentioned above, the composition also includes a polymer. Although not intending to be bound by theory, the polymer or polymer copper/silica nanocomposite may increase the solubility of the composition, enhance the film-forming characteristic of the composition, and/or enhance the adherence characteristics of the composition, while not retarding the antimicrobial characteristics of the composition. In an embodiment, the polymer can include one or more of the following: polyacrylamide, polyvinyl alcohol, polyvinyl pyrolidone, polyethyleneimine, polyethylene glycol, polypropylene glycol, polyacrylic acid, dextran, chitosan, alginate, and a combination thereof. In an embodiment, the ratio of copper/silica nanocomposite to polymer is about 0.1:1 to 3:1 or about 0.5:1 to 2:1. The polymer was added to Cu/Silica nanogel after acid mediated TEOS hydrolysis in acidic conditions. The pH was then raised to about 8 to 9. Based on HRTEM results, the Cu/Silica nanogel integrity remained intact after polymer addition. Therefore, the polymer stabilized Cu/silica nanogel material at higher pHs (e.g., about 6 to 9) by surface interacting with Cu//silica nanogel via intermolecular forces.

In an embodiment, a silica precursor material to make the copper/silica nanocomposite can be made by mixing a silane compound (e.g., alkyl silane, tetraethoxysilane (TEOS), tetramethoxysilane, sodium silicate, or a silane precursor that can produce silicic acid or silicic acid like intermediates and a combination of these silane compounds) with a copper precursor compound (e.g. copper hydroxide and the like)), in an acidic medium (e.g., acidic water). In an embodiment, the pH can be adjusted to about 1.0 to 3.5 using a mineral acid such as nitric acid or hydrochloric acid. In an embodiment, the weight ratio of the silica precursor material to the copper precursor compound can be about 0.1:1 to 3:1. After mixing for a period of time (e.g., about 30 minutes to a few hours or about 12 to 36 hours), a mixture including silica nanoparticles with the copper nanoparticles can be formed. Subsequently, the medium can be brought to a pH of about 7 and held for a time period (e.g., a few hours to a day) to form a silica nanoparticle gel, where the silica nanoparticles are interconnected. In an embodiment, the copper nanoparticles can be part of the interconnection of the silica nanoparticles and/or dispersed within the matrix, while copper ions can be dispersed within the matrix as well. Next a polymer can be added to the mixture having an acidic pH. The mixture is stirred for about 12 to 36 hours. Subsequently, the pH is raised to about 4 using a base to form the composition. This process can be performed using a single reaction vessel or can use multiple reaction vessels.

In an embodiment, after the composition is disposed on the surface, the structure may have an antimicrobial characteristic that is capable of killing a substantial portion of the microorganisms (e.g., bacteria such as *E. coli, B. subtilis* and *S. aureus*) on the surface of the structure and/or inhibits or substantially inhibits the growth of the microorganisms on the surface of the structure. The phrase "killing a substantial portion" includes killing at least about 70%, at least about 80%, at least about 90%, at least about 95%, or at least about 99% of the microorganism (e.g., bacteria) on the surface that the composition is disposed on, relative to structure that does not have the composition disposed thereon. The phrase "substantially inhibits the growth" includes reducing the growth of the microorganism (e.g., bacteria) by at least about 70%, at least about 80%, at least about 90%, at least about 95%, or at least about 99% of the microorganisms on the surface that the composition is disposed on, relative to a structure that does not have the composition disposed thereon.

As mentioned above, embodiments of the present disclosure are effective for the treatment of diseases affecting plants such as citrus plants and trees. In an embodiment, the composition can function as an antibacterial and/or antifungal, specifically, treating, substantially treating, preventing or substantially preventing, plant diseases such as citrus greening (HLB) and citrus canker diseases. The copper can be released from the composition so that it can act as an antibacterial and/or antifungal for a period of time (e.g., from application to days to months). The design of the composition facilitates uniform plant surface coverage or substantially uniform plant surface coverage. In an embodiment, the composition that is applied to plants can have a superior adherence property in various types of exposure to atmospheric conditions such as rain, wind, snow, and sunlight, such that it is not substantially removed over the time frame of the release of the copper. In an embodiment, the composition has a reduced phytotoxic effect or is non-phytotoxic to plants and reduced environmental stress due to minimal Cu content.

Embodiments of the present disclosure can applied on the time frames consistent with the release of the copper, and these time frames can include from the first day of application to about a week, about a month, about two months, about three months, about four months, about five months, about six months, about seven month, or about eight months.

EXAMPLES

Example:
Copper Silica Polymer Nanocomposite:
Materials and Methodology:
Materials:

Copper Hydroxide (65% Metallic Cu)—Supplied by Gowan Company (GWN 10202)

Copper Hydroxide (61% Metallic Cu)—Supplied by Gowan Company (GWN 10316)

Hydrochloric Acid (conc HCL)—Fisher Scientific-Technical Grade CAS #7647-01-0

Sodium Hydroxide (1M & 4M NaOH)—Amresco ACS Grade CAS #1310-73-2

Tetraethylorthosilicate (TEOS)—Gelest Inc—CAS #78-10-4
Polyacrylamide (PAAm) (50% wt)—Aldrich—Catalog #434949, MW Avg 10,000, CAS #9003-05-8

Polyvinylpyrrolidone (PVP) (40 & 50% w/w)—Acros Organics—MW 8000, CAS #9003-39-8

Ethanol (ETOH) (95%) (190 Proof)—Decon Laboratories Inc, Ethyl Alcohol CAS #64-17-5

Deionized $H_2O$—Barnstead Nanopure Diamond

Methodology:

SG 0001 (GWN 10227)

2.895 g of Cu $(OH)_2$ (65% Metallic Cu) was added to 15 mL of EtOH along with 40 mL of deionized $H_2O$. This mixture was set to stir while slowly adding 6 mL of conc. HCL. An additional 303.8 mL of DI $H_2O$ was added and left to stir for 30 mins to ensure all the Cu $(OH)_2$ was completely dissolved. After ensuring the Cu $(OH)_2$ was completely dissolved, 2.7 mL of TEOS was added dropwise and left to stir for 16-24 hrs. PAAm was then measured out and 112.5 mL was added to the stirring mixture and left for 16-24 hrs. At completion of stirring, 5 mL of 1M NaOH was used to raise the pH to 4.05. The mixture was left to stir for 6-12 hrs before use.

Cu $(OH)_2$=2.895 g, 65% Metallic Cu=1.88175 g,
(1.88175/485.4 ml)×1000=3.877 g/L Cu Specific Gravity=1.0222

SG0005 (GWN 10308)

2.775 g of Cu $(OH)_2$ (65% Metallic Cu) was added to 15 mL of EtOH along with 40 mL of deionized $H_2O$. This mixture was set to stir while slowly adding 6 mL of conc. HCL. An additional 294.5 mL of DI $H_2O$ was added and left to stir for 30 mins to ensure all the Cu $(OH)_2$ was completely dissolved. After ensuring the Cu $(OH)_2$ was completely dissolved, 2.7 mL of TEOS was added dropwise and left to stir for 16-24 hrs. PAAm was then measured out and 82.5 mL was added to the stirring mixture and left for 16-24 hrs. At completion of stirring, 17.8 mL of 1M NaOH was used to raise the pH to 4.08. The mixture was left to stir for 6-12 hrs before use.

Cu $(OH)_2$=2.775 g, 65% Metallic Cu=1.80375 g,
(1.80375/458.5 ml)×1000=3.934 g/L Cu Specific Gravity=1.0208

SG0015 (GWN 10309)

2.85 g of Cu $(OH)_2$ (65% Metallic Cu) was added to 15 mL of EtOH along with 40 mL of deionized $H_2O$. This mixture was set to stir while slowly adding 6 mL of conc. HCL. An additional 291 mL of DI $H_2O$ was added and left to stir for 30 mins to ensure all the Cu $(OH)_2$ was completely dissolved. After ensuring the Cu $(OH)_2$ was completely dissolved, 2.7 mL of TEOS was added dropwise and left to stir for 16-24 hrs. PVP (40% w/w) was then measured out and 97.5 mL was added to the stirring mixture and left for 16-24 hrs. At completion of stirring, 18 mL of 1M NaOH was used to raise the pH to 4.2. The mixture was left to stir for 6-12 hrs before use.

Cu $(OH)_2$=2.85 g, 65% Metallic Cu=1.8525 g,
(1.8525/470.2 ml)×1000=3.937 g/L Cu Specific Gravity=1.0086

SG0017 (GWN 10310)

2.85 g of Cu $(OH)_2$ (65% Metallic Cu) was added to 15 mL of EtOH along with 40 mL of deionized $H_2O$. This mixture was set to stir while slowly adding 6 mL of conc. HCL. An additional 292.6 mL of DI $H_2O$ was added and left to stir for 30 mins to ensure all the Cu $(OH)_2$ was completely dissolved. After ensuring the Cu $(OH)_2$ was completely dissolved, 2.7 mL of TEOS was added dropwise and left to stir for 16-24 hrs. PAAm was then measured out and 90 mL was added to the stirring mixture and left for 16-24 hrs. At completion of stirring, 16.8 mL of 1M NaOH was used to raise the pH to 4.08. The mixture was left to stir for 6-12 hrs before use.

Cu $(OH)_2$=2.85 g, 65% Metallic Cu=1.8525 g,
(1.8525/463.1 ml)×1000=4 g/L Cu Specific Gravity=1.0271

SG0018 (GWN 10311)

2.895 g of Cu $(OH)_2$ (65% Metallic Cu) was added to 15 mL of EtOH along with 40 mL of deionized $H_2O$. This mixture was set to stir while slowly adding 6 mL of conc. HCL. An additional 296 mL of DI $H_2O$ was added and left to stir for 30 mins to ensure all the Cu $(OH)_2$ was completely dissolved. After ensuring the Cu $(OH)_2$ was completely dissolved, 2.7 mL of TEOS was added dropwise and left to stir for 16-24 hrs. PVP (40% w/w) was then measured out and 135 mL was added to the stirring mixture and left for 16-24 hrs. At completion of stirring, 17 mL of 1M NaOH was used to raise the pH to 4.2. The mixture was left to stir for 6-12 hrs before use.

Cu $(OH)_2$=2.895 g, 65% Metallic Cu=1.88175 g,
(1.88175/511.7)×1000=3.677 g/L Cu Specific Gravity=1.0130

SG0020 (GWN 10327)

10.416 g of Cu $(OH)_2$ (65% Metallic Cu) was added to 15 mL of EtOH along with 73 mL of deionized $H_2O$. This mixture was set to stir while slowly adding 18 mL of conc. HCL. After ensuring the Cu $(OH)_2$ was completely dissolved, 9.45 mL of TEOS was added dropwise and left for 6-12 hrs. PAAm was then measured out and 393.75 mL was added to the stirring mixture and left for 16-24 hrs. At completion of stirring, 12 mL of 1M NaOH was used to raise the pH to 3.8. The mixture was left to stir for 6-12 hrs before use.

Cu $(OH)_2$=10.416 g, 65% Metallic Cu=6.7704 g,
(6.7704/521.2 ml)×1000=12.99 g/L Cu Specific Gravity=1.1541

SG0021 (GWN 10328)

5.356 g of Cu $(OH)_2$ (65% Metallic Cu) was added to 15 mL of EtOH along with 34.6 mL of deionized $H_2O$. This mixture was set to stir while slowly adding 12 mL of conc. HCL. After ensuring the Cu $(OH)_2$ was completely dissolved, 4.99 mL of TEOS was added dropwise and left to stir for 6-12 hrs. PAAm was then measured out and 207.68 mL was added to the stirring mixture and left for 16-24 hrs. At completion of stirring, 36 mL of 1M NaOH was used to raise the pH to 3.75. The mixture was left to stir for 6-12 hrs before use.

Cu $(OH)_2$=5.356 g, 65% Metallic Cu=3.4814 g,
(3.4814/310.27)×1000=11.22 g/L Cu Specific Gravity=1.1445

SG0022 (GWN 10332)

12.92 g of Cu (OH)$_2$ (61% Metallic Cu) was added to 15 mL of EtOH along with 22 mL of conc. HCL slowly. After ensuring the Cu (OH)$_2$ was completely dissolved, 11.1 mL of TEOS was added dropwise and left to stir for 6-12 hrs. PAAm was then measured out and 300 mL was added to the stirring mixture and left for 16-24 hrs. At completion of stirring, ~71.78 mL of 1M NaOH was used to raise the pH to 4.33. The mixture was left to stir for 6-12 hrs before use.
Cu (OH)$_2$=12.92 g, 61% Metallic Cu=7.8812 g, (7.8812/419.88)×1000=18.77 g/L Cu Specific Gravity=1.154

SG0022M 75 mL of SG0022 (GWN 10332) (pH 4.33) was raised to pH 8.67 using 34 mL of 1M NaOH. The new Cu content was determined to be 12.92 g/L. The mixture was left to stir for 6-12 hrs before use.
Specific Gravity=1.091

SG0023

4.5 g of Cu (OH)$_2$ (61% Metallic Cu) was added to 10 mL of EtOH along with 10 mL of conc. HCL slowly. After ensuring the Cu (OH)$_2$ was completely dissolved, 3.7 mL of TEOS was added dropwise and left to stir for 6 hrs. PAAm was then measured out and 100 mL was added to the stirring mixture and left for 16-24 hrs. At completion of stirring, ~27 mL of 4M NaOH was used to raise the pH to 8.82. The mixture was left to stir for 6-12 hrs before use.
Cu (OH)$_2$=4.5 g, 61% Metallic Cu=2.745 g, (2.745/151 ml)×1000=18.18 g/L Cu Specific Gravity=1.145

SG0024

4.5 g of Cu (OH)$_2$ (61% Metallic Cu) was added to 14 mL of EtOH along with 8 mL of conc. HCL slowly. After ensuring the Cu (OH)$_2$ was completely dissolved, 3.7 mL of TEOS was added dropwise and left to stir for 6 hrs. PVP (50% w/w) was then measured out and 100 mL was added to the stirring mixture and left for 16-24 hrs. At completion of stirring, ~19.4 mL of 4M NaOH was used to raise the pH to 8.38. The mixture was left to stir for 6-12 hrs before use.
Cu (OH)$_2$=4.5 g, 61% Metallic Cu=2.745 g, (2.745/145.1)×1000=18.92 g/L Cu Specific Gravity=1.094

Table 1 is a summary of the Nanoformulation Compositions.

| Formulation Code | Metallic Cu (g/L) | TEOS (mL) | PVP (40/50% wt)(mL) | PAAm (50% wt) (mL) | pH | Specific Gravity |
|---|---|---|---|---|---|---|
| SG0001 | 3.877 | 2.7 | NA | 112.5 | 4.05 | 1.0222 |
| SG0005 | 3.934 | 2.7 | NA | 82.5 | 4.08 | 1.0208 |
| SG0015 | 3.937 | 2.7 | 97.5 | NA | 4.2 | 1.0086 |
| SG0017 | 4.0 | 2.7 | NA | 90 | 4.08 | 1.0271 |
| SG0018 | 3.677 | 2.7 | 135 | NA | 4.2 | 1.0130 |
| SG0020 | 12.99 | 9.45 | NA | 393.75 | 3.8 | 1.1541 |
| SG0021 | 11.22 | 4.99 | NA | 207.68 | 3.75 | 1.1445 |
| SG0022 | 18.77 | 11.1 | NA | 300 | 4.33 | 1.1540 |
| SG0022M | 12.92 | 11.1 | NA | 300 | 8.67 | 1.091 |
| SG0023 | 18.18 | 3.7 | NA | 100 | 8.82 | 1.145 |
| SG0024 | 18.92 | 3.7 | 100 | NA | 8.38 | 1.094 |

Copper Silica Polymer Nanocomposite:
Characterization:

Scanning Electron Microscopy (SEM) and High-Resolution Transmission Electron Microscopy (HRTEM) was conducted to observe the morphology, crystallinity and confirm the elemental composition of the 2 nanoformulations (SG0023 and SG0024). SEM was conducted on a Zeiss Ultra-55 FEG SEM using mica wafers. The TEM was conducted on a FEI Tecnai F30 using carbon filmed gold grids.

Figure 2:
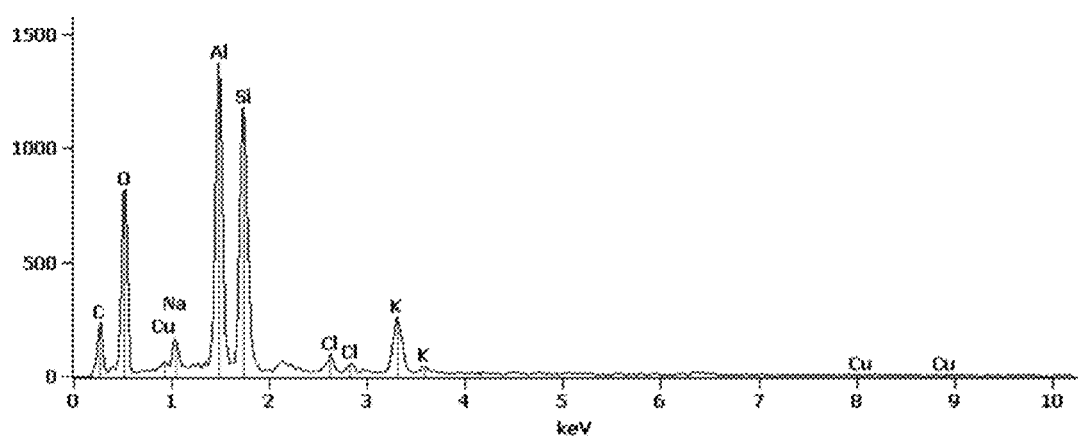
FIG. 2 illustrates EDS of elements in sample from FIG. 1 within SG0023. Cu and Si confirmed.
Figure 3:
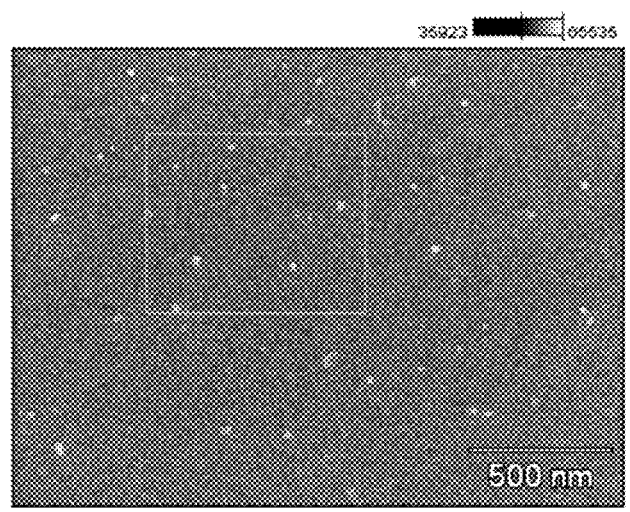
FIG. 3 illustrates spherical clusters of material within SG0023 seen in SEM.
Figure 4:
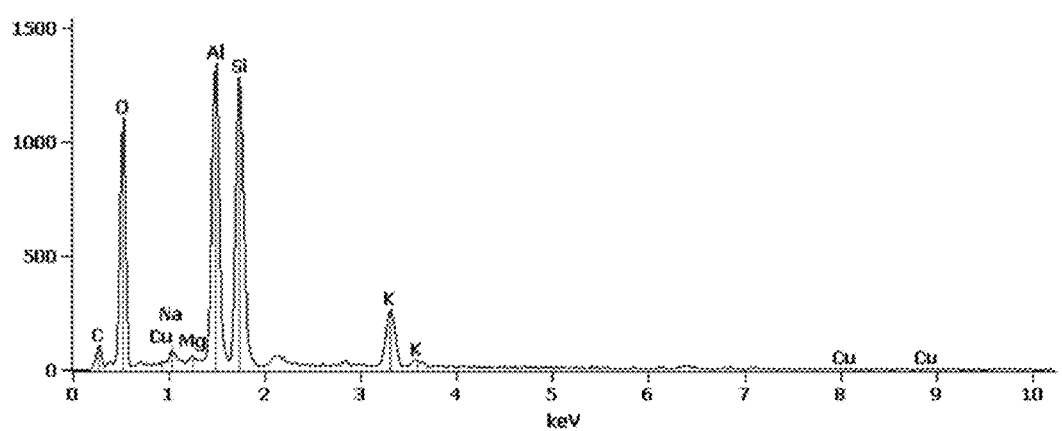
FIG. 4 illustrates EDS of elements in sample from FIG. 3 within SG0023. Cu and Si confirmed.
Figure 5:
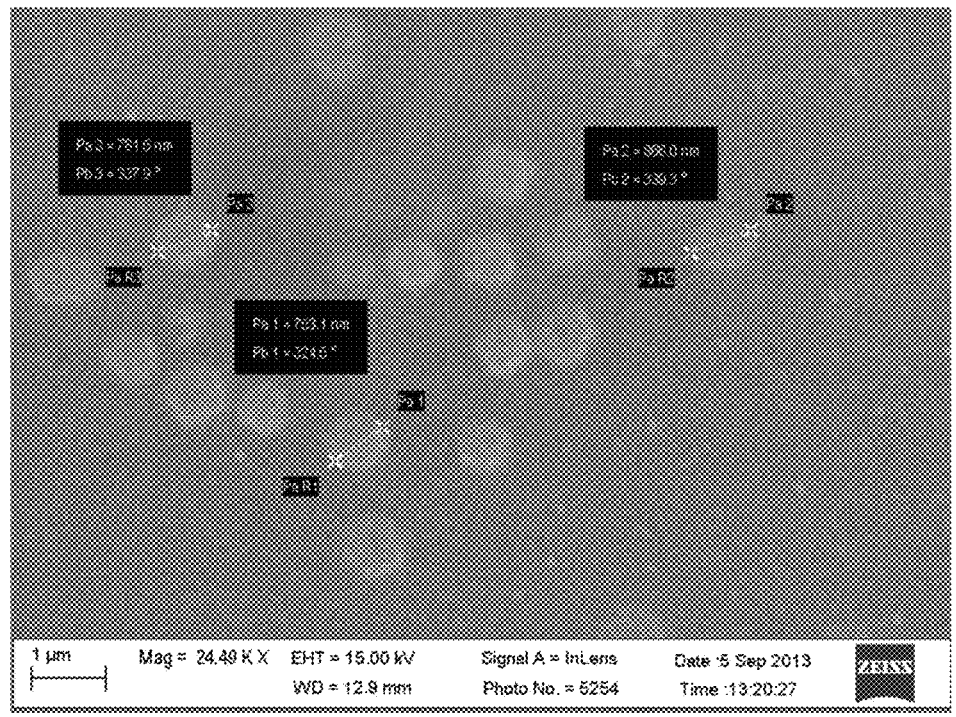
FIG. 5 illustrates spherical clusters of material within SG0023 seen in SEM.
Figure 6:
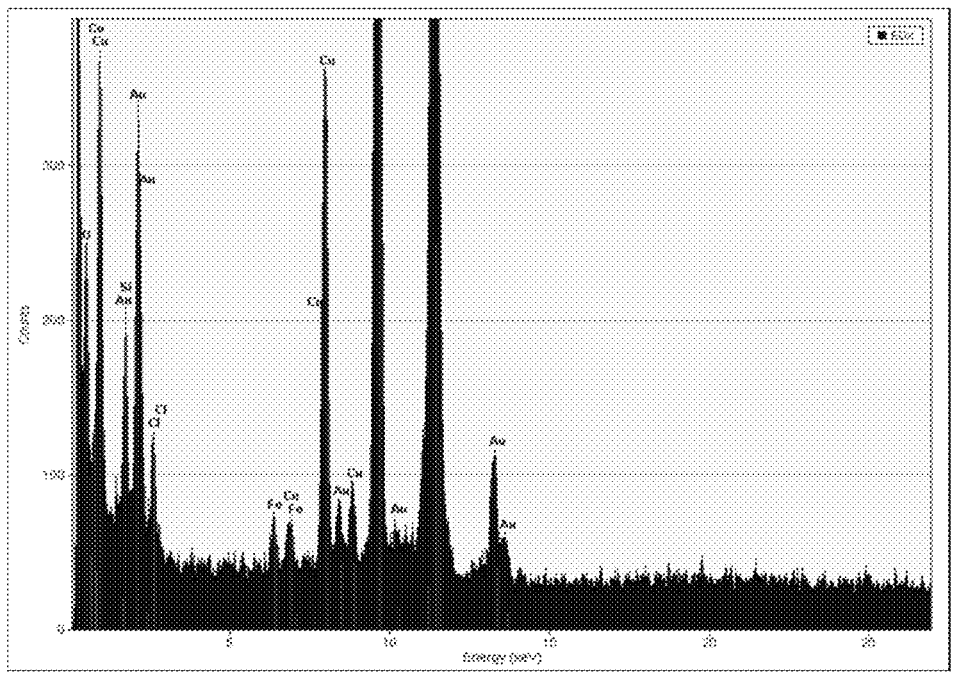
FIG. 6 illustrates EDS of SG0023 sample seen in HRTEM. Cu and Si confirmed.
Figure 7:
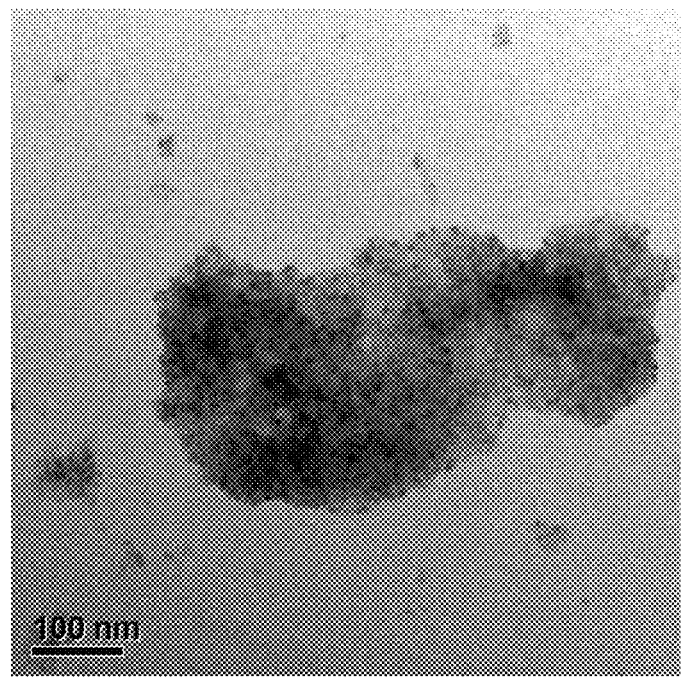
FIG. 7 illustrates high-resolution, low magnification image of SG0023 showing areas of dark contrast indicating electron rich material.
Figure 8:
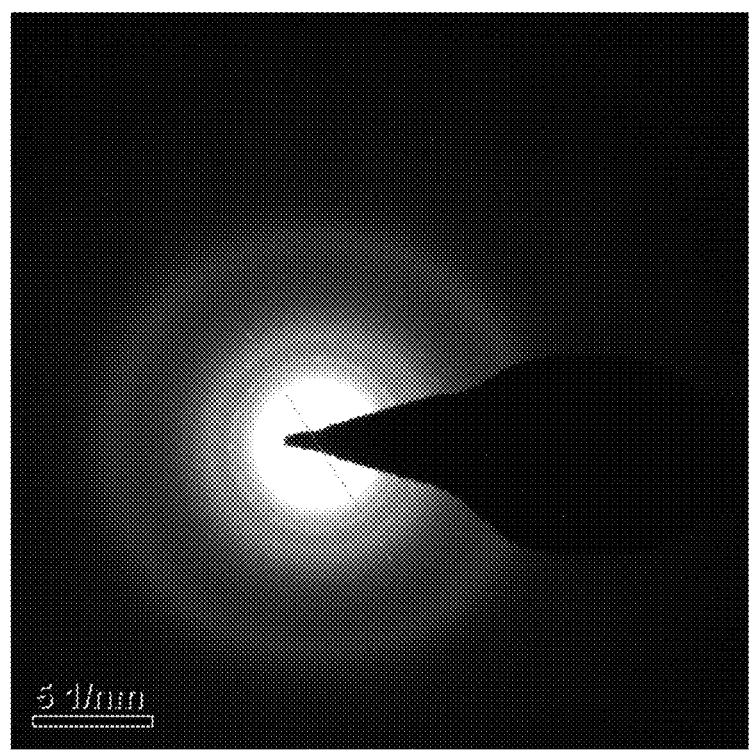
FIG. 8 illustrates SAED image of SG0023 confirming crystalline nature.
Figure 9:
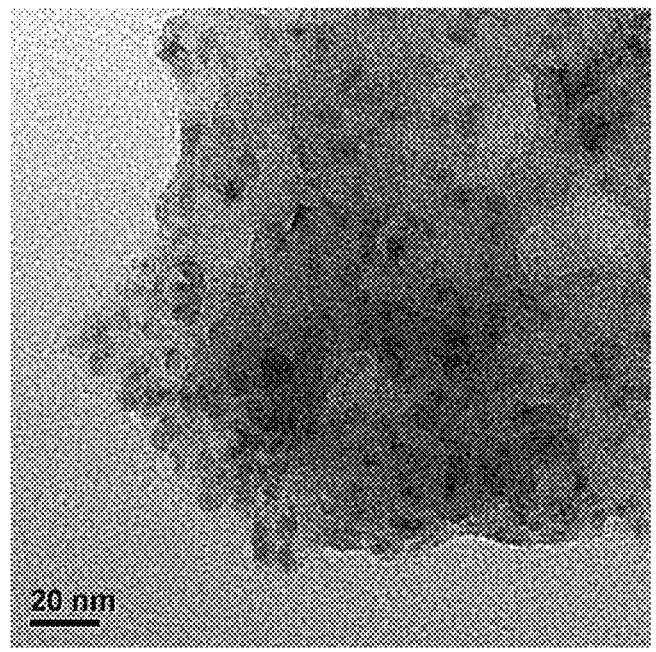
FIG. 9 illustrates high-resolution, high magnification image of SG0023 showing areas of dark contrast indicating electron rich material.
Figure 10:
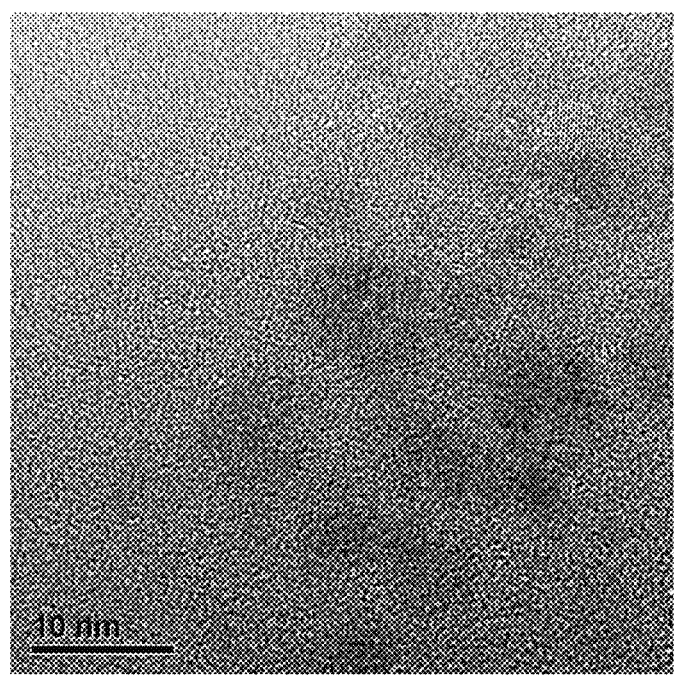
FIG. 10 illustrates high-resolution, high magnification image of SG0023 showing areas of dark contrast indicating electron rich material. Cu Crystallites can be seen with sizes between 4-8 nm. Lattice spacing of crystallites determined as 2.76 Å, 2.27 Å, 3.03 Å, 1.78 Å and 2.54 Å.
Figure 11:
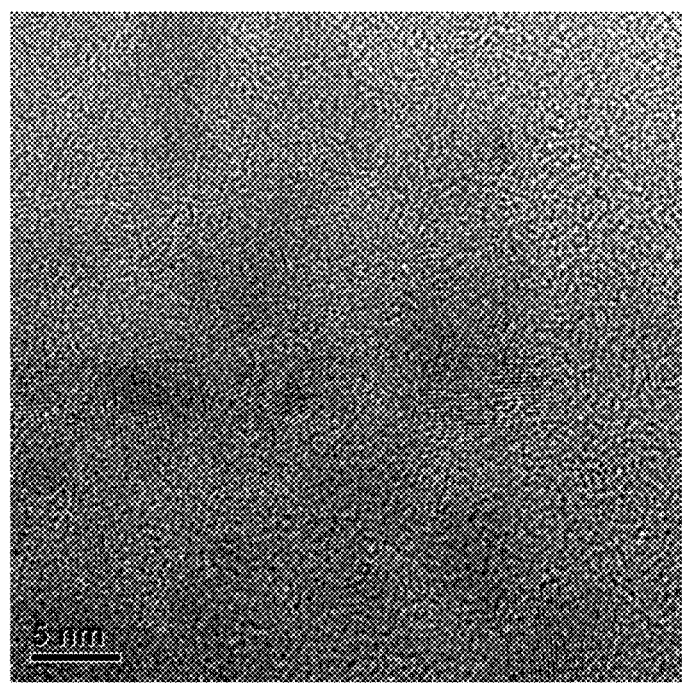
FIG. 11 illustrates high-resolution, high magnification image of SG0023 showing areas of dark contrast indicating electron rich material. Cu Crystallites can be seen with sizes between 4-8 nm. Lattice spacing of crystallites determined as 2.76 Å, 2.27 Å, 3.03 Å, 1.78 Å and 2.54 Å.

In the SG0023 formulation, the elemental composition was confirmed using Energy Dispersive Spectroscopy (EDS) while doing SEM AND HRTEM. The EDS confirmed the presence of our sample by identifying the Cu and Si in the material (FIGS. 2, 4, and 6). SEM images showed spherical clusters within the larger silica matrix, with aggregates ranging from 50-600 nm (FIGS. 1, 3, and 5). HRTEM exhibited a well dispersed material with areas of light and dark contrast of electron rich material (FIGS. 7 and 9). The crystallinity of the Cu materials were confirmed using Selected Area Electron Diffraction (SAED) (FIG. 8). Crystallites of Cu were clearly visible at high magnification. Determination of the lattice revealed spacing of 2.76 Å, 2.27 Å, 3.03 Å, 1.78 Å and 2.54 Å. These values correspond with CuO, CuO, Cu$_2$O, Cu and CuO respectively (FIGS. 10 and 11).

Figure 12:
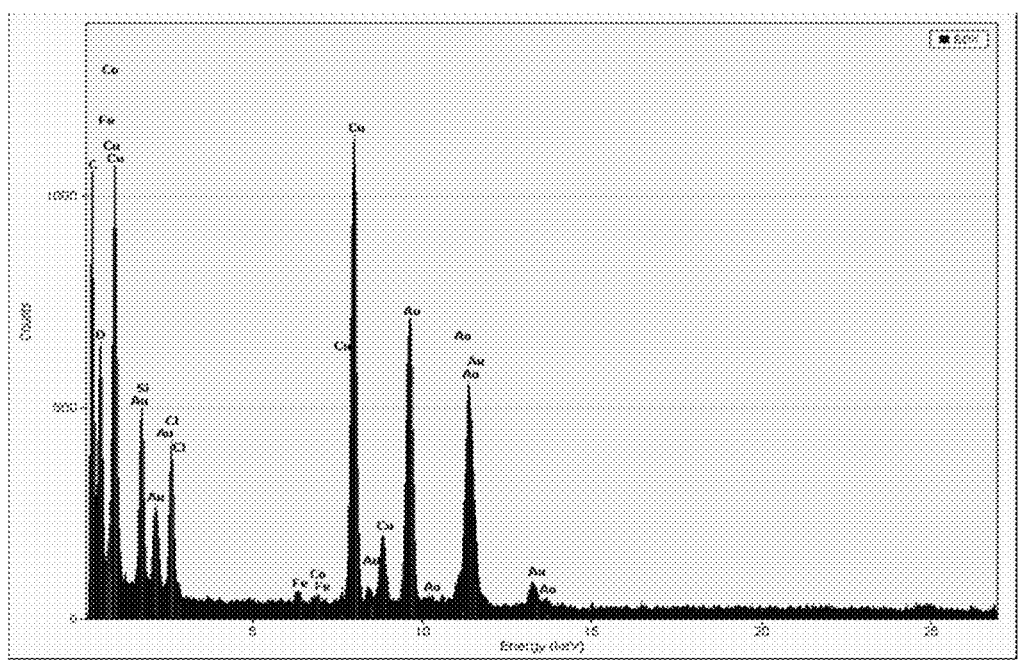
FIG. 12 illustrates EDS of SG0024 sample seen in HRTEM. Cu and Si confirmed.
Figure 13:
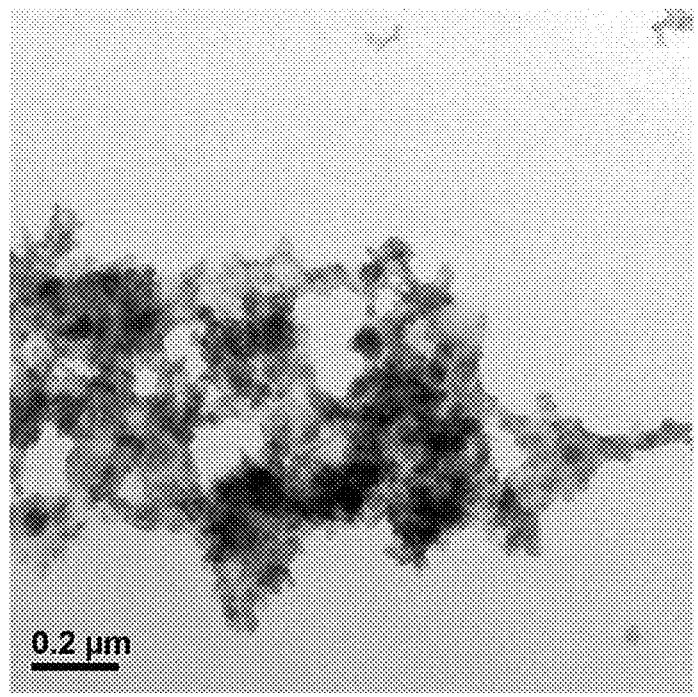
FIG. 13 illustrates high-resolution, low magnification image of SG0024 showing areas of dark contrast indicating electron rich material.
Figure 14:
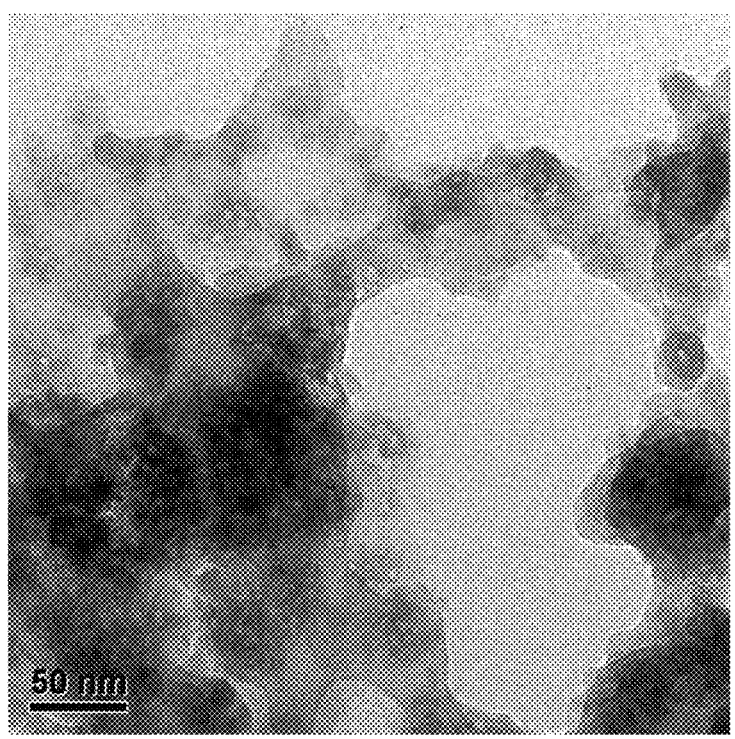
FIG. 14 illustrates high-resolution, low magnification image of SG0024 showing areas of dark contrast indicating electron rich material.
Figure 15:
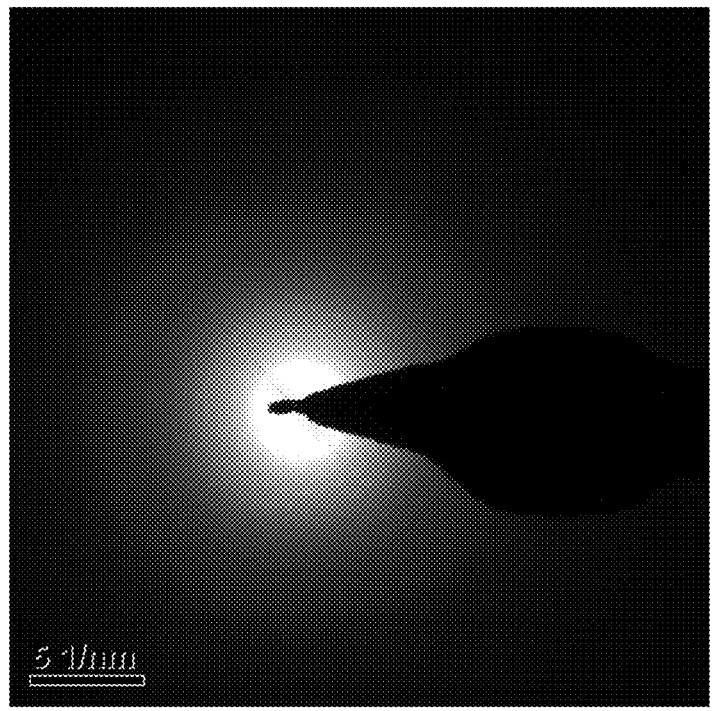
FIG. 15 illustrates SAED image of SG0024 confirming crystalline nature.
Figure 16:
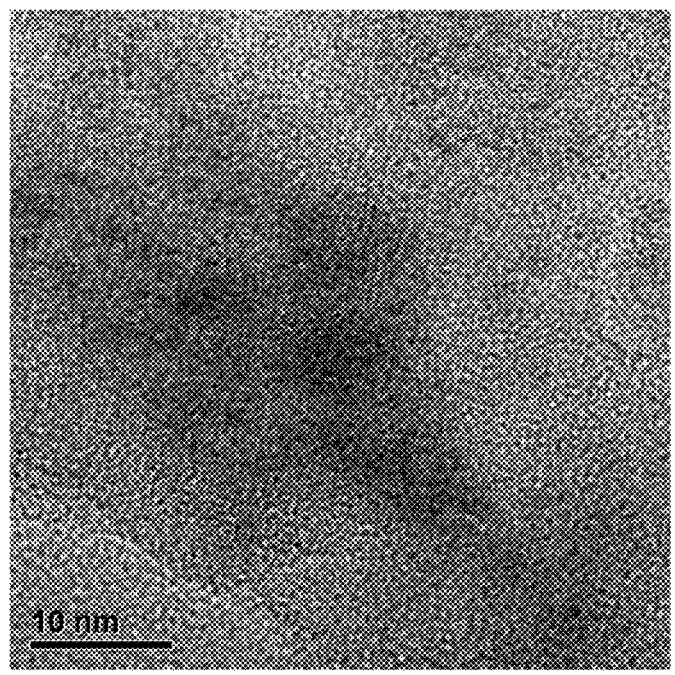
FIG. 16 illustrates high-resolution, high magnification image of SG0024 showing areas of dark contrast indicating electron rich material. Cu Crystallites can be seen with sizes between 4-8 nm. Lattice spacing of crystallites determined as 2.75 Å, 2.45 Å and 2.26 Å.
Figure 17:
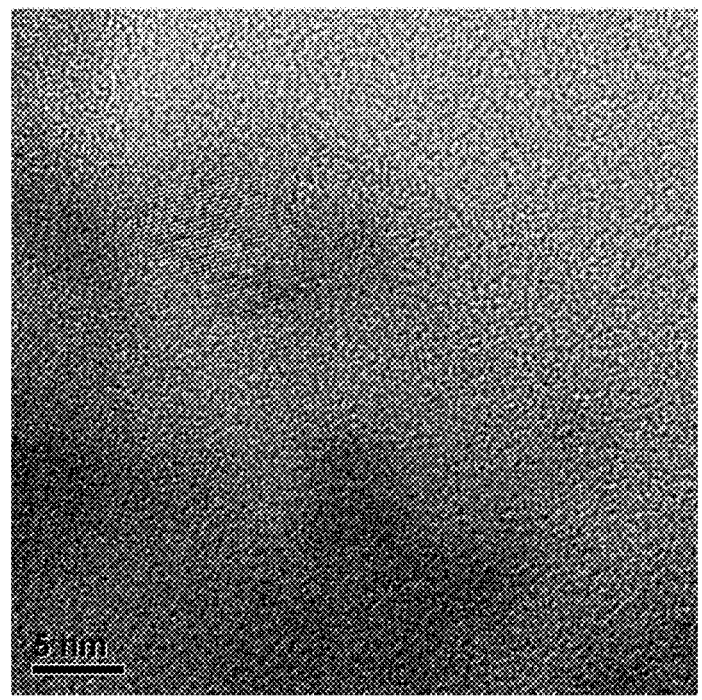
FIG. 17 illustrates high-resolution, high magnification image of SG0024 showing areas of dark contrast indicating electron rich material. Cu Crystallites can be seen with sizes between 4-8 nm. Lattice spacing of crystallites determined as 2.75 Å, 2.45 Å and 2.26 Å.
Figure 18:
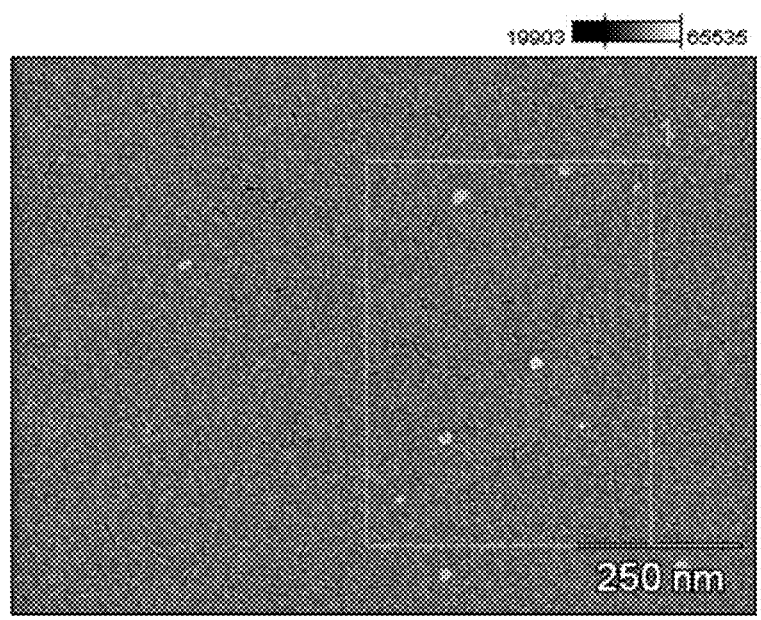
FIG. 18 illustrates spherical clusters of material within SG0024 seen in SEM.
Figure 19:
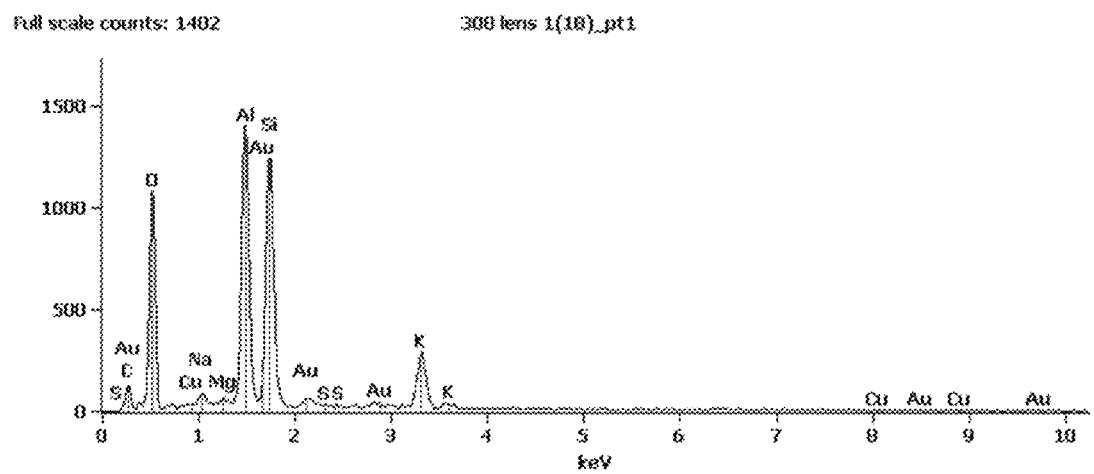
FIG. 19 illustrates EDS of elements in sample from FIG. 18 within SG0024. Cu and Si confirmed.
Figure 20:
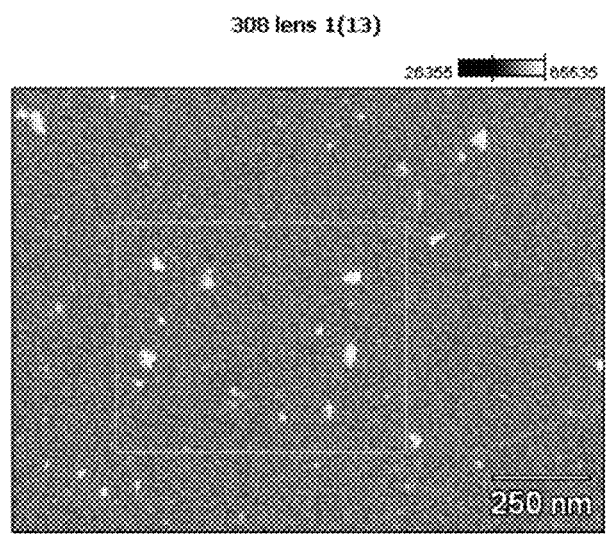
FIG. 20 illustrates clusters of material within SG0024 seen in SEM.
Figure 21:
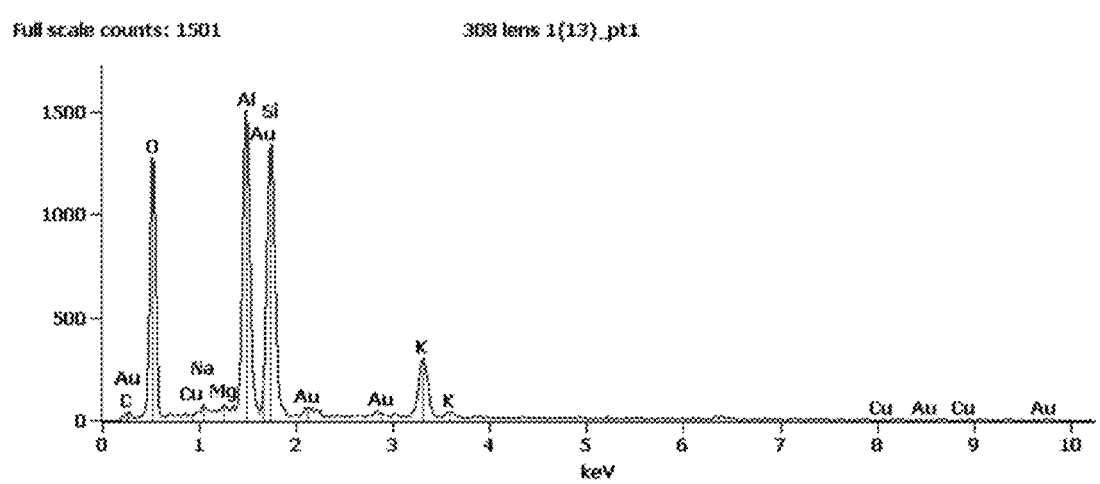
FIG. 21 illustrates EDS of elements in sample from FIG. 20 within SG0024. Cu and Si confirmed.

In the SG0024 formulation, the elemental composition was confirmed using Energy Dispersive Spectroscopy (EDS) while doing SEM AND HRTEM. The EDS confirmed the presence of our sample by identifying the Cu and Si in the material (FIGS. 12, 19, and 21). SEM images showed spherical clusters within the larger silica matrix, with aggregates ranging from 50-300 nm (FIGS. 18 and 20). HRTEM exhibited a well dispersed material with areas of light and dark contrast of electron rich material (FIGS. 13 and 14). The crystallinity of the Cu materials were confirmed using Selected Area Electron Diffraction (SAED) (FIG. 15). Crystallites of Cu were clearly visible at high magnification. Determination of the lattice revealed spacing of 2.75 Å, 2.45 Å and 2.26 Å. These values correspond with CuO, Cu$_2$O and CuO respectively (FIGS. 16 and 17).

Phytotoxicity Studies:

Phytotoxicity studies were conducted to observe plant injury on exposure to our nanoformulations. Studies were conducted on *Vinca* sp obtained from the local Home Depot and kept in a mini-greenhouse under conditions ≥80 F temperature and ≥40% humidity. Plants were obtained and allowed to acclimatize for 24 hrs before formula application. Nanoformulations were applied at specific Cu concentrations between 6 and 8 am before temperatures rose too high. Plants were observed for tissue damage at 24, 48 and 72 hr time points.

It was seen that SG0001, SG0005, SG0015, SG0017, SG0018, SG0020, SG0021 and SG0022 (FIGS. 22 and 23) caused moderate to high levels of plant tissue damage. SG0022M, SG0023, SG0024 and Kocide 3000 (FIGS. 22 and 24) exhibited no plant tissue damage at any Cu concentrations after 72 hrs. The reason for no toxicity was due to higher pHs in SG0022M, SG0023, SG0024 and Kocide 3000. Higher pHs lead to oxidation of Cu ions into less soluble Cu oxide and hydroxide.

Antimicrobial Studies:

Antimicrobial studies were conducted to ascertain the effectiveness of synthesized nanoformulations in comparison to the Kocide 3000 control. Studies conducted were growth inhibition assays using Muller Hinton 2 (MH2) broth and determination of the Minimum Inhibitory Concentration (MIC) following the guidelines of the Clinical and Laboratory Standards Institute (CLSI). Studies were conducted against gram negative *E. coli* sp.

Figure 26:
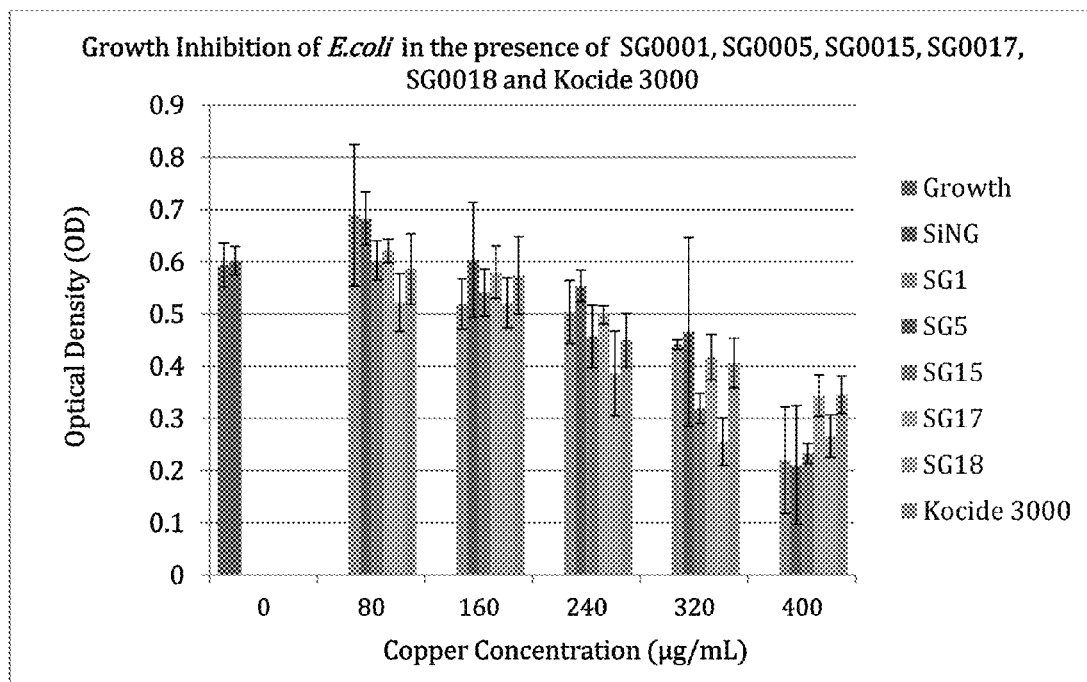
FIG. 26 is a graphs that illustrates the growth inhibition of *E. coli* in the presence of SG0001, SG0005, SG0015, SG0017, SG0018 and Kocide 3000.
Figure 27:
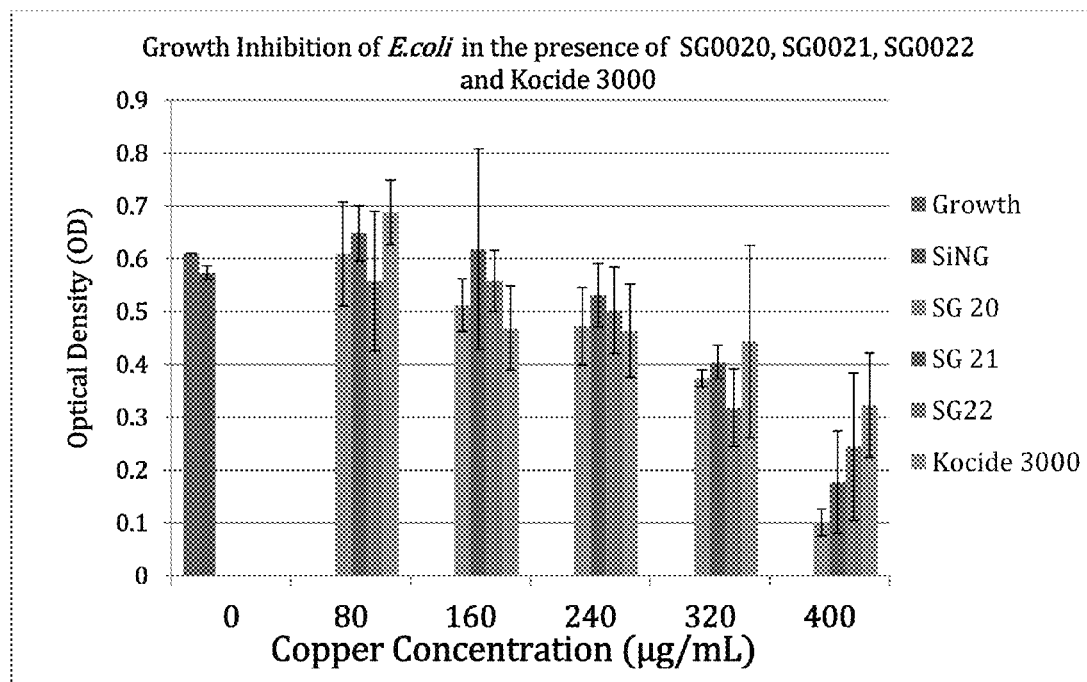
FIG. 27 is a graph that illustrates the growth inhibition of *E. coli* in the presence of SG0020, SG0021, SG0022 and Kocide 3000.
Figure 28:
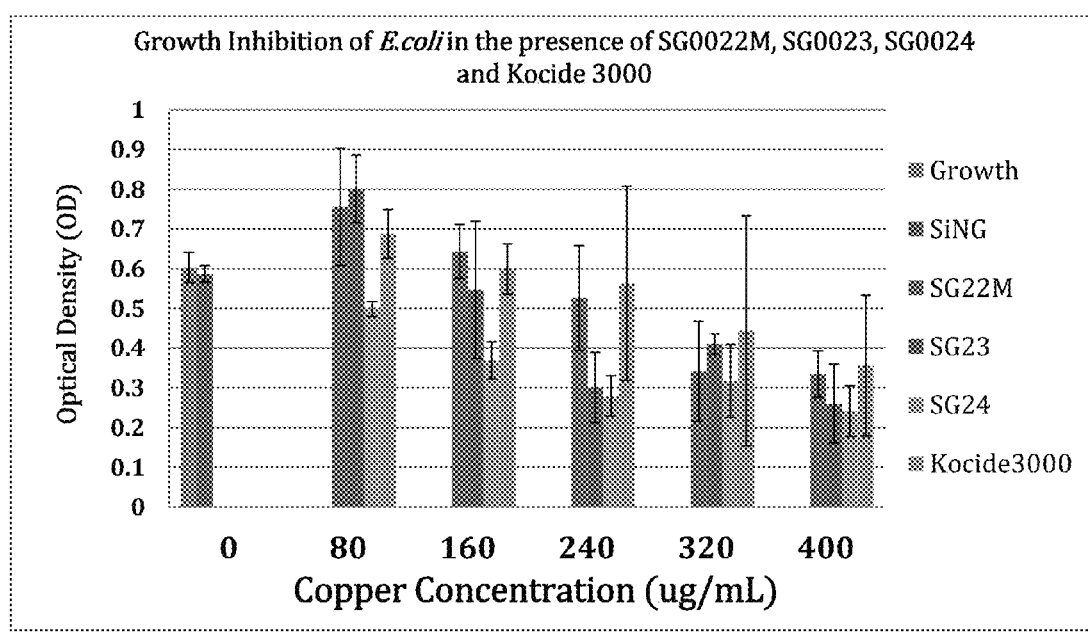
FIG. 28 is a graph that illustrates the growth inhibition of *E. coli* in the presence of SG0022M, SG0023, SG0024 and Kocide 3000.

Growth inhibition studies showed reduced bacterial growth as Cu concentration increased. Results indicated improved antimicrobial efficacy in Cu nanoformulations in relation to the Kocide 3000 control (FIGS. 26, 27, and 28). The MIC of Cu nanoformulations was found to be 437.5 µg/mL for SG0001, SG0005, SG0015, SG0017 and SG0018. The MIC for SG0020, SG0021, SG0022, SG0022M, SG0023 and SG0024 was 500 µg/mL while Kocide 3000 had a value of 1000 µg/mL (FIG. 25). This reinforces the higher antimicrobial efficacy of our Cu nanoformulations.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A composition, comprising:
    a copper/silica nanocomposite having a silica gel matrix that includes copper from one or more of copper nanoparticles and copper ions; and
    a polymer selected from the group consisting of polyacrylamide, polyvinyl alcohol, polyvinyl pyrrolidone, polyethylene glycol, polypropylene glycol, dextran, chitosan, alginate, and a combination thereof, wherein the composition has an antimicrobial characteristic and the composition also has a lower phytotoxicity than another composition including the copper/silica nanocomposite but not the polymer.

2. The composition of claim 1, wherein the ratio of copper/silica nanocomposite to polymer is about 0.1:1 to 3:1.

3. The composition of claim 1, wherein the composition is transparent or translucent to visible light.

4. The composition of claim 1, wherein the copper is about 1 microgram (ug)/mL to 20 milligram (mg)/mL of the copper/silica-polymer nanocomposite.

5. The composition of claim 1, wherein the copper nanoparticles have a diameter of about 5 to 20 nm.

6. The composition of claim 1, wherein the polymer is polyvinyl alcohol.

7. The composition of claim 1, wherein the polymer is polyvinyl pyrrolidone.

8. The composition of claim 1, wherein the polymer is polyethylene glycol or polypropylene glycol.

9. The composition of claim 1, wherein the polymer is chitosan.

10. The composition of claim 1, wherein the polymer is alginate.

11. The composition of claim 1, wherein the polymer is dextran.

12. The composition of claim 1, wherein the polymer is polyacrylamide.

13. A method of making the composition of claim 1, comprising:
    mixing a silica precursor compound and a copper precursor compound in a solvent to form a copper/silica nanocomposite having a silica gel matrix that includes copper from one or more of copper nanoparticles and copper ions; and
    mixing the copper/silica nanocomposite with a polymer to provide the composition that has a phytotoxicity than another composition including the copper/silica nanocomposite but not the polymer.

14. The method of claim 13, wherein:
    the mixing of the silica precursor compound and the copper precursor compound includes adjusting a water solvent pH to less than about 7 and holding for about 12 to about 36 hours;
    the mixing of the copper/silica nanocomposite with the polymer is then undertaken at an acidic pH for about 12 to about 36 hours; and
    the pH is then raised to about 4 to about 10 to form the composition.

15. A method, comprising;
    treating a surface of a substrate with the composition of claim 1.

16. The method of claim 15 wherein: the treating the surface comprises forming a liquid layer of the composition upon the substrate; and the substrate is a foliage substrate from a tree or a plant.

* * * * *